United States Patent [19]
Bonastre et al.

[11] Patent Number: 5,886,201
[45] Date of Patent: Mar. 23, 1999

[54] QUATERNIZED FATTY ACID TRIETHANOLAMINE ESTER SALTS WITH IMPROVED SOLUBILITY IN WATER

[75] Inventors: Nuria Bonastre, Barbara del Valles; Joaquim Bigorra Llosas, Sabadell; Rafael Pi Subirana, Granollers, all of Spain

[73] Assignee: Henkel Kommanditgesellschaft auf Aktien, Duesseldorf, Germany

[21] Appl. No.: 624,589

[22] PCT Filed: Sep. 29, 1994

[86] PCT No.: PCT/EP94/03253

§ 371 Date: Apr. 8, 1996

§ 102(e) Date: Apr. 8, 1996

[87] PCT Pub. No.: WO95/10500

PCT Pub. Date: Apr. 20, 1995

[30] Foreign Application Priority Data

Oct. 8, 1993 [DE] Germany .......................... 43 34 365.1

[51] Int. Cl.$^6$ .................................................. C07C 101/00
[52] U.S. Cl. .......................... 554/110; 554/103; 554/108; 554/114
[58] Field of Search ..................................... 884/110, 103, 884/108, 114

[56] References Cited

U.S. PATENT DOCUMENTS 4,830,771  5/1989  Rubeck et al. ........................... 252/8.8

FOREIGN PATENT DOCUMENTS 22248905  10/1972  Germany .
WO 9101295  2/1991  WIPO .

OTHER PUBLICATIONS

CED/Kongress, Sitges, 1993, p. 59 (translation).

*Primary Examiner*—Samuel Barts
*Assistant Examiner*—Deborah D Carr
*Attorney, Agent, or Firm*—Ernest G. Szoke; Wayne C. Jaeschke; Real J. Grandmaison

[57] ABSTRACT

A process for producing quaternized fatty acid triethanolamine ester salts having improved solubility in water, by esterifiying a fatty acid mixture containing a) 40% to 60% by weight of linear fatty acids containing 6 to 22 carbon atoms, and b) 60% to 40% by weight of branched fatty acids containing 6 to 22 carbon atoms, wherein the esterifying step is conducted with triethanolamine or ethylene oxide adducts of triethanolamine, and the resultant esters are then quaternized.

12 Claims, No Drawings

QUATERNIZED FATTY ACID TRIETHANOLAMINE ESTER SALTS WITH IMPROVED SOLUBILITY IN WATER

This application is a 371 of PCT/EP94/03253 filed Sep. 29, 1994.

BACKGROUND OF THE INVENTION

1. Field of the Invention

This invention relates to quaternized fatty acid triethanolamine ester salts ("esterquats") with improved solubility in water which are obtained by esterifying selected mixtures of linear and branched fatty acids with a triethanolamine component and then quaternizing the resulting esters by methods known per se, to a process for their production, to the use of the new esterquats for the production of surface-active formulations and to the use of the fatty acid mixtures for the production of water-soluble esterquats.

2. Discussion of Related Art

Quaternized fatty acid triethanolamine ester salts, so-called "esterquats", are cationic surfactants which are acquiring increasing significance by virtue of their excellent fabric-softening properties and their high ecotoxicological compatibility. The publications by O. Ponsati in C.R. CED Congress, Barcelona, 1992, page 167 and R. Puchta in C.R. CED Congress, Sitges, 1993, page 59, are cited as representative of the literature available on the subject.

The esterquats are normally prepared by a two-stage process in which triethanolamine is first partly esterified with fatty acids and the reaction product is then quaternized with methyl chloride or preferably dimethyl sulfate in isopropyl alcohol. Low-viscosity concentrates of the esterquats in isopropyl alcohol with a solids content of up to 85% by weight can be obtained in this way. However, products of satisfactory odor, i.e. alcohol-free products, are required for many applications, particularly in the cosmetics field. If the isopropyl alcohol is removed after quaternization, commercial esterquats are solid which is detrimental to their processability. Another disadvantage is that the known water-free commercially available esterquats are difficult to disperse in water and that, in particular, the production of concentrates is not possible without the assistance of auxiliaries.

Now, the problem addressed by the present invention was to provide new esterquats which would have low viscosities in water-free form, would be readily processable to water-containing concentrates and would exhibit advantageous performance properties.

DESCRIPTION OF THE INVENTION

The present invention relates to quaternized fatty acid triethanolamine ester salts with improved solubility in water corresponding to formula (I):

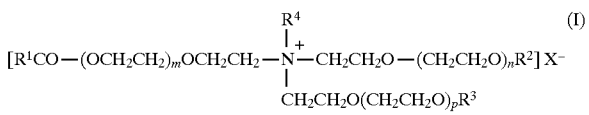

in which 40 to 60% by weight of $R^1CO$ is a linear acyl radical containing 6 to 22 carbon atoms and 60 to 40% by weight is a branched acyl radical containing 6 to 22 carbon atoms, $R^2$ and $R^3$ independently of one another represent hydrogen or have the same meaning as $R^1CO$, $R^4$ is an alkyl radical containing 1 to 4 carbon atoms or a $(CH_2CH_2O)_qH$ group, m, n and p together stand for 0 or for numbers of 1 to 12, q is a number of 1 to 12 and X is halide, alkyl sulfate or alkyl phosphate.

Extensive studies conducted by applicants have shown that, although esterquats based on branched fatty acids have low viscosities, they do not have a softening effect. Conversely, esterquats based on linear fatty acids are distinguished by good fabric-softening properties, but at the same time are solid and cannot readily be dispersed in water-free form. It has now surprisingly been found that starting materials for the production of esterquats which flow freely in water-free form and which are soluble in water in highly concentrated form are available within a narrow mixing ratio between linear and branched fatty acids. The new esterquats show advantageous performance properties and can be processed, for example, to low-viscosity high-strength fabric softener concentrates.

The present invention also relates to a process for the production of quaternized fatty acid triethanolamine ester salts with improved solubility in water, in which fatty acid mixtures containing a) 40 to 60% by weight of linear fatty acids containing 6 to 22 carbon atoms and b) 60 to 40% by weight of branched fatty acids containing 6 to 22 carbon atoms are esterified with triethanolamine or with adducts of ethylene oxide with triethanolamine and the resulting esters are quaternized by methods known per se.

Fatty acids

The choice of the fatty acids and their mixing ratio is of particular importance to the essence of the present invention.

Component a) may be selected, for example, from caproic acid, caprylic acid, capric acid, lauric acid, myristic acid, palmitic acid, palmitoleic acid, stearic acid, oleic acid, elaidic acid, petroselic acid, linoleic acid, linolenic acid, elaeosteric acid, ricinoleic acid, 12-hydroxystearic acid, arachic acid, gadoleic acid, behenic acid and erucic acid and from the technical mixtures thereof obtained, for example, in the pressure hydrolysis of fats and oils, for example palm oil, palm kernel oil, coconut oil, sunflower oil and rapeseed oil from old and new plants, olive oil, cottonseed oil, peanut oil, meadowfoam oil, castor oil, lard oil and beef tallow.

Technical mixtures of these fatty acids with at most one double bond, if any, are preferably used. It is particularly preferred to use palm oil fatty acid, tallow fatty acid and/or new sunflower oil fatty acid. It is pointed out in connection with new sunflower oil fatty acid that it contains at least 80% by weight of oleic acid. Contrary to the usual biassed view that unsaturated cis-fatty acids are more or less unsuitable as a basis for the production of esterquats with favorable fabric-softening properties, new sunflower oil fatty acid—either on its own or in admixture with other linear fatty acids—has proved to be particularly advantageous.

In one particular embodiment of the invention, therefore, mixtures of new sunflower oil fatty acid and palm oil fatty acid in a ratio by weight of 40:60 to 60:40 and preferably 50:50 are used as component a).

Component b) is selected from branched fatty acids such as, for example, 2-ethyl hexanoic acid, isotridecanoic acid, isopalmitic acid and/or isostearic acid. It has proved to be best to use short-chain branched fatty acids to achieve optimal solubility and long-chain branched fatty acids to achieve particularly good fabric-softening properties. It is within the ability of the expert—if necessary—to balance out the properties of both types by suitable mixing without having to become involved in inventive activity in the process.

The preferred ratio between linear and branched fatty acids is of the order of 50:50 and, more particularly, in the range from 45:50 to 55:45 parts by weight.

Esterification and quaternization

The esterification of the fatty acids with the triethanolamine or the ethylene oxide/triethanolamine adduct may be carried out by methods known per se, cf. international patent application WO 91/01295 (Henkel). The fatty acids and the triethanolamine component may normally be used in a molar ratio of 1.2:1 to 1.9:1 and preferably 1.4:1 to 1.8:1. Suitable esterification catalysts are in particular hypophosphorous acid or alkali metal salts thereof.

The quaternization is carried out in known manner, preferably with alkyl halides, alkyl sulfates, alkyl phosphates or alkylene oxides. Methyl chloride, dimethyl sulfate or ethylene oxide is preferably used. Isopropyl alcohol, for example, may be used as solvent, being removed on completion of the reaction. If necessary, the esterquats may be bleached with hydrogen peroxide and stabilized by addition of antioxidants.

Commercial Applications

The esterquats according to the invention are free-flowing in water-free form and may be processed to water-containing concentrates with an active substance content of up to 50% by weight and preferably from 20 to 35% by weight. They have good fabric-softening and antistatic properties.

Accordingly, the present invention relates to their use for the production of surface-active formulations, for example laundry detergents, dishwashing detergents, cleaning formulations and fabric softeners and hair-care and body-care products, in which they may be present in quantities of 1 to 50% by weight and preferably in quantities of 5 to 30% by weight, based on the particular formulation.

Finally, the present invention relates to the use of fatty acid mixtures containing a) 40 to 60% by weight of linear fatty acids containing 6 to 22 carbon atoms and b) 60 to 40% by weight of branched fatty acids containing 6 to 22 carbon atoms for the production of quaternized fatty acid triethanolamine ester salts with improved solubility in water.

The following Examples are intended to illustrate the invention without limiting it in any way.

EXAMPLES

I. Fatty acid mixtures used

A) 50% by weight new sunflower oil fatty acid
   50% by weight 2-ethyl hexanoic acid
B) 25% by weight palm oil fatty acid
   25% by weight new sunflower oil fatty acid
   50% by weight 2-ethyl hexanoic acid
C) 50% by weight palm oil fatty acid
   50% by weight isostearic acid
D) 30% by weight new sunflower oil fatty acid
   20% by weight palm oil fatty acid
   50% by weight isostearic acid
E) 100% by weight palm oil fatty acid
F) 100% by weight sunflower oil fatty acid
G) 100% by weight 2-ethyl hexanoic acid
H) 100% by weight isostearic acid Fatty acid mixtures A to D correspond to the invention while fatty acids E to H are intended for comparison.

II. Production Examples a) Esterification

Quantities of 1.49 moles of fatty acid mixtures A to D and E to H and 149 g (1 mole) of triethanolamine and 1.4 g of 50% by weight hypophosphorous acid were introduced into a 1 liter three-necked flask equipped with a stirrer, internal thermometer and distillation bridge. The reaction mixture was then heated under a reduced pressure of 40 mbar to a temperature of 160° C. until the acid value was below 5 (4 hours). The crude fatty acid triethanolamine ester was then cooled, the reaction mixture was relieved of pressure and 1 liter of air was passed through for 15 minutes with continuous stirring.

b) Quaternization

A mixture of 45 g (0.1 mole) of the ester from a) in 150 ml of isopropyl alcohol was introduced into and heated with stirring to 45° C. in a 500 ml three-necked flask equipped with a stirrer, dropping funnel and reflux condenser. 12 g (0.095 mole) of dimethyl sulfate were added dropwise over a period of 2 h. After the addition, the mixture was stirred for another 2 h at 60° C., the solvent was removed and unreacted DMS was destroyed by addition of 0.4 g (0.005 mole) of glycine.

III. Application Examples

The solubility and viscosity of the esterquats were evaluated in water-free form and in the form of a 32% by weight dilute solution.

To determine their fabric-softening effect, cotton fabric (molleton) which was hard through repeated washing was treated by padding with 32% by weight aqueous solutions or dispersions of the products. The treatment was carried out under the following conditions:

Concentration : 30 g/l of the 32% by weight products

Liquor uptake : approx. 80% by weight, based on dry fabric

Drying : 3 minutes at 180° C.

The softening effect was subjectively evaluated by a test panel of 6 experienced examiners on a scale of (++)=very good softening effect, (+)=satisfactory softening effect, (−)= minimal softening effect to (−−)=no softening effect.

The results are set out in Table 1:

TABLE 1

Viscosity, solubility and softening effect

| Ex. | FA | Water-Free Product | Concentrate, 32% by Weight | Vis. mPa · s | SE |
|---|---|---|---|---|---|
| 1 | A | Free-flowing | Clear solution | 342 | + |
| 2 | B | Free-flowing | Clear solution | 1190 | + |
| 3 | C | Free-flowing | Opaque solution | 4560 | + |
| 4 | D | Free-flowing | Opaque solution | 550 | + |
| C1 | E | Solid | Viscous paste | — | ++ |
| C2 | F | Solid | Viscous paste | — | + |
| C3 | G | Free-flowing | Clear solution | — | −− |
| C4 | H | Solid | Viscous paste | — | − |

Legend:
FA = Fatty acid basis
Vis. = Viscosity of 32% product; Brookfield, 20° C., 200 r.p.m., spindle 1–2
SE = Softening effect

What is claimed is:

1. Quaternized fatty acid triethanolamine ester salts having improved solubility in water corresponding to formula (I):

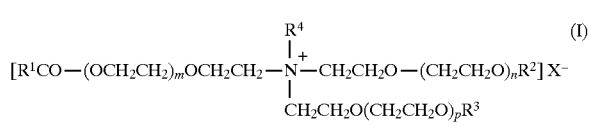

in which

40% to 60% by weight of $R^1CO$ is a linear acyl radical containing 6 to 22 carbon atoms and 60% to 40% by weight is a branched acyl radical containing 6 to 22 carbon atoms, $R^2$ and $R^3$ independently of one another represent hydrogen or have the same meaning as $R^1CO$, $R^4$ is an alkyl radical containing 1 to 4 carbon atoms or a $(CH_2CH_2O)_qH$ group, m, n and p together represent 0 or a number of I to 12, q is a number of 1 to 12, and X is halide, alkyl sulfate or alkyl phosphate.

2. Quaternized fatty acid triethanolamine ester salts as in claim 1 wherein said linear acyl radical comprises a linear fatty acid selected from the group consisting of sunflower oil fatty acid, palm oil fatty acid, tallow fatty acid, and mixtures thereof.

3. Quaternized fatty acid triethanolamine ester salts as in claim 2, wherein said linear fatty acid comprises a mixture of sunflower oil fatty acid and palm oil fatty acid present in a weight ratio of 40:60 to 60:40.

4. Quaternized fatty acid triethanolamine ester salts as in claim 1 wherein said branched acyl radical comprises a branched fatty acid selected from the group consisting of 2-ethyl hexanoic acid, isotridecanoic acid, isopalmitic acid, isostearic acid, and mixtures thereof.

5. Quaternized fatty acid triethanolamine ester salts as in claim 1 wherein said linear acyl radical and said branched acyl radical are present in a molar ratio of 1.2:1 to 1.9:1 with respect to triethanolamine.

6. The process of producing quaternized fatty acid triethanolamine ester salts having improved solubility in water, comprising esterifiying a fatty acid mixture comprising a) 40% to 60% by weight of linear fatty acids containing 6 to 22 carbon atoms, and b) 60% to 40% by weight of branched fatty acids containing 6 to 22 carbon atoms, said esterifying step being conducted with triethanolamine or ethylene oxide adducts of triethanolamine, and quaternizing the resultant esters.

7. A process as in claim 6 wherein said linear fatty acids are selected from the group consisting of sunflower oil fatty acid, palm oil fatty acid, tallow fatty acid, and mixtures thereof.

8. A process as in claim 6 wherein said linear fatty acids comprise sunflower oil fatty acid and palm oil fatty acid present in a weight ratio of 40:60 to 60:40.

9. A process as in claim 6 wherein said branched fatty acids are selected from the group consisting of 2-ethyl hexanoic acid, isotridecanoic acid, isopalmitic acid, isostearic acid, and mixtures thereof.

10. A process as in claim 6 wherein said linear fatty acids and said branched fatty acids are present in a molar ratio of 1.2:1 to 1.9:1 with respect to triethanolamine.

11. A process as in claim 6 wherein said quaternizing step is carried out with alkyl halides, alkyl sulfates, alkyl phosphates or alkylene oxides.

12. A process as in claim 6 further including adding the product thereof to a surface-active composition.

* * * * *